(12) United States Patent
Pomeranz et al.

(10) Patent No.: US 6,241,666 B1
(45) Date of Patent: *Jun. 5, 2001

(54) ABLATION CATHETER TIP WITH A BUFFER LAYER COVERING THE ELECTRODE

(75) Inventors: Mark L. Pomeranz, Los Gatos; N. Parker Willis, Atherton; Richard E. Riley, Palo Alto, all of CA (US)

(73) Assignee: Cardiac Pathways Corp., Sunnyvale, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/887,731

(22) Filed: Jul. 3, 1997

(51) Int. Cl.[7] ......................................................... A61B 5/04
(52) U.S. Cl. .............................. 600/381; 606/32; 606/41; 607/101
(58) Field of Search ........................... 606/32, 34, 37–41, 606/45–50; 600/372, 381; 604/508, 19, 22, 264; 602/1, 2, 115, 116, 101

(56) References Cited

U.S. PATENT DOCUMENTS

| | | |
|---|---|---|
| 3,044,836 | 7/1962 | Conlon . |
| 4,850,351 | 7/1989 | Herman et al. . |
| 4,945,912 | 8/1990 | Langberg . |
| 4,979,948 | 12/1990 | Geddes et al. . |
| 5,122,138 | * 6/1992 | Manwaring ............................. 606/46 |
| 5,191,883 | 3/1993 | Lennox et al. . |
| 5,230,349 | 7/1993 | Langberg . |
| 5,234,004 | 8/1993 | Hascoet et al. . |
| 5,236,413 | 8/1993 | Feiring . |
| 5,281,213 | 1/1994 | Milder et al. . |
| 5,334,193 | 8/1994 | Nardella . |
| 5,342,357 | 8/1994 | Nardella . |

(List continued on next page.)

FOREIGN PATENT DOCUMENTS

| | | |
|---|---|---|
| 30 38 885 A1 | 5/1982 | (DE) . |
| 0 499 491 A2 | 8/1992 | (EP) . |
| 0 539 125 A1 | 4/1993 | (EP) . |
| 1466248 | 3/1967 | (FR) . |
| 1690786 A1 | 11/1991 | (SU) . |
| WO90/07909 | 7/1990 | (WO) . |
| WO 94/08519 | 4/1994 | (WO) . |
| WO95/34346 | 6/1995 | (WO) . |
| WO 96/00041 | 1/1996 | (WO) . |
| WO 96/00042 | 1/1996 | (WO) . |

OTHER PUBLICATIONS

Borggrefe, M.; Budde, T.; Podczeck, A.; Breithardt, G.; High Frequency Alternating Current Ablation of an Accessory Pathway in Humans, JACC vol. 10 No. 3 pp.576–582 (Sep. 1987).

Abstracts 17A, JACC, vol. 11 No. 2, 3 pgs. (Feb. 1988).

*Primary Examiner*—Glenn K. Dawson
(74) *Attorney, Agent, or Firm*—Stallman & Pollock LLP

(57) ABSTRACT

An ablative catheter assembly whose electrode is completely covered by a buffer layer. The buffer layer prevents areas of high current density at the surface of the catheter tip, which helps to reduce popping and clotting. The buffer layer may be in the form of a conductive fluid (such as saline solution) pumped into a cavity surrounding the electrode. In this case, the conductive fluid couples the electrode to the surrounding tissue so that RF energy will pass from the electrode to the tissue, thereby effecting ablation. Also, the buffer layer may be in the form of a porous coating which covers an electrode tip. In this case, blood or fluid which infuses the porous coating couples the electrode tip to the surrounding tissues to be ablated.

20 Claims, 4 Drawing Sheets

U.S. PATENT DOCUMENTS

| | | |
|---|---|---|
| 5,348,554 * | 9/1994 | Imran et al. .................... 607/105 |
| 5,368,597 | 11/1994 | Pagedas . |
| 5,383,876 | 1/1995 | Nardella . |
| 5,423,811 | 6/1995 | Imran et al. . |
| 5,443,470 | 8/1995 | Stern et al. . |
| 5,454,370 | 10/1995 | Avitall . |
| 5,487,385 | 1/1996 | Avitall . |
| 5,505,730 | 4/1996 | Edwards . |
| 5,520,684 * | 5/1996 | Imran ................................ 606/41 |
| 5,569,241 | 10/1996 | Edwards . |
| 5,584,872 | 12/1996 | Lafontaine et al. . |
| 5,647,871 * | 7/1997 | Levine et al. .................... 606/45 |
| 5,879,348 | 3/1999 | Owens et al. .................... 606/41 |
| 5,891,136 | 4/1999 | McGee et al. .................... 606/41 |

* cited by examiner

ABLATION CATHETER TIP WITH A BUFFER LAYER COVERING THE ELECTRODE

BACKGROUND OF THE INVENTION

The present invention relates to ablation catheter tip assemblies. More specifically, the present invention relates to RF ablative tip catheters wherein an RF electrode is covered with a buffer layer covering the metal electrode.

DESCRIPTION OF THE RELATED ART

Supraventricular tachycardia, ventricular tachycardia, and atrial fibrillation are conditions in the heart generally known as arrhythmias. During an arrhythmia, abnormal electrical signals are generated in the endocardial tissue which cause irregular beating of the heart. One method used to treat these arrhythmias involves creating lesions within the chambers of the heart on the endocardium. These lesions are intended to stop the irregular beating of the heart by creating barriers between regions of the tissue. These barriers halt the passage through the heart of the abnormal currents generated in the endocardium.

RF energy can be used to ablate tissue, such as tissue in the heart, to form the appropriate lesion barriers to stop the flow of abnormal currents. One conventional apparatus for performing RF ablation is an RF ablation catheter with an ablative catheter tip.

An internal electrode (i.e., the ablative tip of an RF ablation catheter) is placed inside the body, adjacent to tissue which is to be ablated. An external electrode is placed on the skin surface. A power supply generates electrical power (generally radio frequency current) which is communicated between the internal electrode and the external electrode so that the RF energy ablates tissue in the vicinity of the internal electrode.

FIGS. 1 and 2 show an RF ablation catheter with an ablative tip. Note that a similar, RF ablation catheter is described in U.S. Pat. No. 5,348,554 to Imran et al., which is incorporated by reference. In the catheter shown in FIG. 1, an RF power supply and controller 76 supplies high frequency energy to the hollow conductive electrode tip 16 of the catheter through a lead wire 31, in order to ablate tissue and/or cause lesions. The hollow tip conducting electrode 16 can be formed of a suitable material such as stainless steel or platinum. The lead wire 31 runs through a central lumen 28 and is physically connected to the conductive tip 16 at juncture 32.

The catheter shown in FIGS. 1 and 2 also includes a flexible elongate member 12, formed of a suitable plastic, such as polyurethane. Disposed on the elongate member 12, near its tip, is a braid 21, which provides kink-resistance and reinforcement. The elongate member 12 may additionally include other conventional elements such as steering wires (not shown).

One problem with RF ablation catheters is clotting. Clotting has been observed to be correlated with denaturizing of the blood with high temperature and/or high current density areas in the vicinity of the catheter tip. Clots of solid organic matter are produced. These clots (or coagulum) are undesirable because they may travel in the blood stream and cause an embolic event.

Another problem in cardiac ablation is the phenomenon of "popping". Popping refers to explosions in the body's tissue which are observed during RF ablation. Popping is generally undesirable because it causes irregularities, such as tears, in the ablated tissue, and therefore it becomes more difficult to precisely control which tissue is ablated. Also, the force of the popping explosions can cause and disperse coagulum. The exact mechanism by which popping occurs has not been fully explained.

In order to reduce the high temperatures at the catheter tip, the catheter in FIG. 1 has a saline circulating system for cooling, which is further discussed below.

The saline circulating system is made up of pumping assembly 10, lumens 26, 27, 28 and cavity 17. The saline circulating system circulates a saline solution through lumen 26 into the cavity 17 which is inside the conductive tip electrode 16. More specifically, the pumping assembly pumps saline solution into lumen 27. The saline solution then flows into cavity 17, where it cools the tip 16. The saline solution then flows back out of the catheter through lumen 26, and back to the pumping assembly 10. The pressure and temperature of the saline solution can be controlled by means which are more fully discussed in U.S. Pat. No. 5,348,554.

While the conventional catheter shown in FIG. 1 has been found to be reasonably effective in preventing hot spots on the catheter tip and resultant overheating of the tissue, popping and clotting can still occur at higher power levels. For example, there is still a high current density at the edge 16a of the conductive tip, which can potentially cause overheating of the tissue.

SUMMARY OF THE INVENTION

An object of the present invention is to provide an ablative catheter assembly which exhibits reduced popping and clotting. It is now believed that popping is caused by ignition of a combination of by-products of the tissue heating and by-products of electrolysis that occurs due to transferring current between the metal tip and electrolytes in blood and tissue. This ignition occurs at areas of high current density near the metal tip where electrolysis occurs. As explained in detail below, especially in view of the foregoing theory of popping, various types of buffer layers on an ablation catheter tip can help to reduce popping by keeping the by-products of the tissue heating away from high current density areas on the metal electrode.

According to some embodiments of the present invention, the buffer layer is a layer of conductive fluid, such as saline solution, which surrounds the metal electrode. The conductive fluid will communicate RF energy from the electrode to the metal catheter tip, while providing a more uniform current density at the exterior surface of the metal catheter tip. This means that combustible products of the ablation reaction which happen to reach the outer surface of the catheter tip will not come into contact with metal at an area of high current density, and will therefore prevent ignition, combustion and popping.

In the fluid buffer layer embodiments, the catheter assembly includes an elongate catheter shaft, a hollow metal tip, a lead wire, and an electrode. The tip covers the distal end of the catheter shaft. A lumen is provided to deliver conductive fluid to the tip. The lead wire is disposed within the catheter shaft. The electrode is connected at an end of the lead wire and is disposed within the hollow tip, spaced away from the inner surface thereof. Because the electrode is spaced away from the surface of the tip (preferably by at least one millimeter) a buffer layer of conductive fluid forms around the electrode.

In some of embodiments which utilize the conductive fluid for a buffer layer, the tip can be formed from a solid material. Preferably, the conductive fluid is circulated from the proximal end of the catheter into the tip and then back out the proximal end of the catheter. In the alternative, the tip can be provided with flushing holes which allow the passage of conductive fluid through the tip and out into the blood/tissue interface. In the embodiments wherein the tip includes flushing holes, the tip can be formed from either a conductive or a nonconductive material. It should be noted that in the fluid buffer layer embodiments, the conductive fluid acts not only as a buffer layer but as a means for cooling the tip.

According to other embodiments of the present invention, a metal catheter tip is coated with a non-conductive, porous, buffer layer. The buffer layer may be made of various materials, such as cellulose, polymeric materials, adhesives, or metallic salts. The buffer layer is porous so that RF energy may be efficiently transferred from the metal catheter tip to the surrounding blood and tissue, while still preventing combustible products of the ablation reaction from reaching high current density areas on the metal tip itself, thereby preventing ignition, combustion and popping.

The embodiments which include a porous buffer layer also include a catheter shaft and a lead wire. The lead wire is connected to a conductive tip electrode mounted at the end of the catheter. The porous, non-conductive buffer layer covers the exterior surface of the tip electrode.

The porous buffer layer is configured so that it will absorb body fluids when the electrode is inserted into the body. The fluids will infuse the buffer layer to a degree sufficient to allow electrical coupling between the exterior surface of the metal electrode and the tissues of the body. In this way, ablation of the tissues can occur despite the intermediate non-conductive buffer layer.

DETAILED DESCRIPTION OF THE PREFERRED EMBODIMENTS

Figures 1, 2:
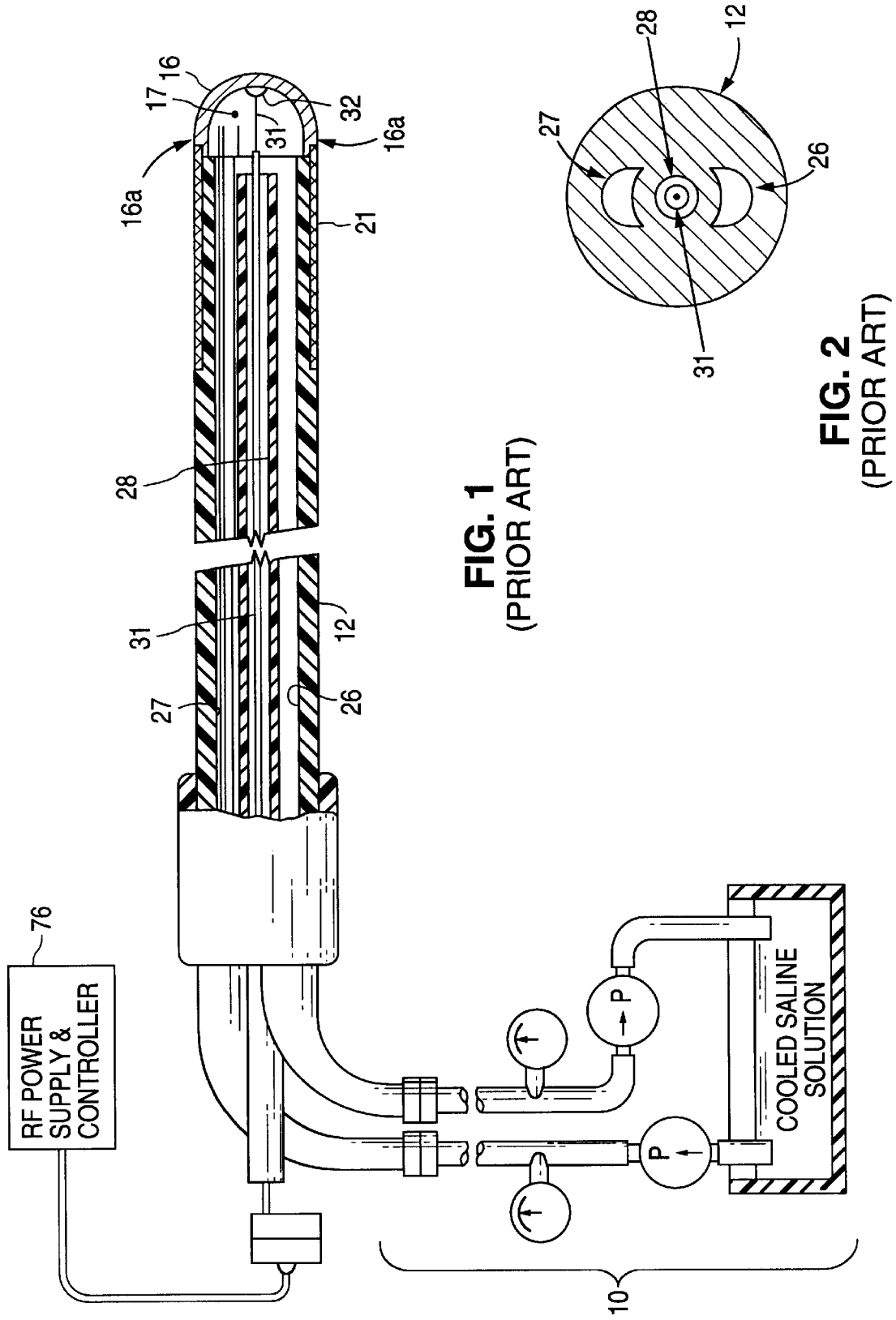
FIG. 1 shows a longitudinal cross-sectional view of conventional saline-cooled ablative tip catheter found in the prior art.
FIG. 2 shows a longitudinal cross-sectional view of the conventional catheter tip shown in FIG. 1.
Figure 3:
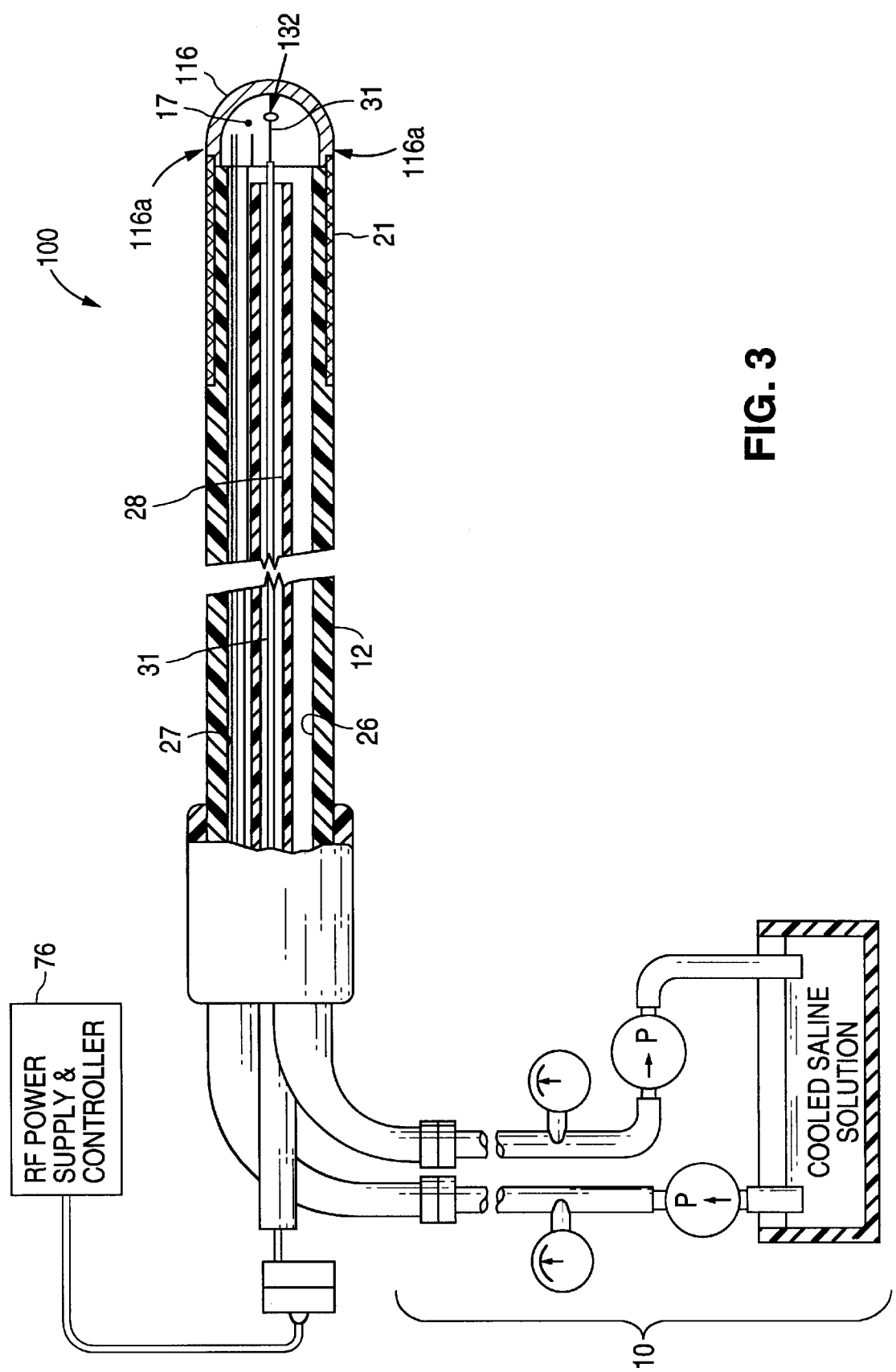
FIG. 3 shows a first embodiment of an ablative tip catheter according to the present invention.

FIG. 3 shows a first embodiment of an ablative catheter 100 according to the present invention. The ablative catheter 100 shown in FIG. 3 has certain elements in common with the catheter shown in FIG. 1. Common elements are denoted by common reference numerals.

In the catheter 100, RF electrical energy (e.g., RF frequency AC current of approximately 500 kHz) is supplied to the electrode 132 via a lead wire 31. The electrode 132 is disposed within the cavity 17 defined by a cup-shaped, rigid metal tip 116. Unlike the prior art catheter of FIG. 1, in this embodiment electrode 132 is spaced away from the interior wall of the metal tip 116 and does not touch the metal tip 116. The electrode 132 is formed of a suitable metal such as stainless or platinum and is suspended within the cavity 17 by the lead wire extrusion 31. Preferably, the electrode 132 is suspended in the vicinity of the center of the cavity, but it may be placed at least as close as 1 millimeter away from the interior wall of the tip 116.

Saline solution is pumped through lumen 26, to the cavity 17 and thence back through lumen 27 by pumping assembly 10. The saline solution in the cavity 17 will communicate RF energy from the electrode 132 to the metal tip 116. The metal tip 116 then communicates the RF energy to adjacent tissues to effect ablation.

Because the electrode 132 is spaced away from the metal tip 116, and because the RF energy is communicated through a buffer layer of saline solution in the cavity 17 in order to get to the tip 116, the tip 116 will have a more uniform current density distribution. This avoids areas of high current density at the exterior surface of the tip 116, especially areas of high current density which otherwise would tend to occur at the edge of the tip 116a if the electrode 132 were in direct contact with the tip. Because the tip 116 does not have areas of high current density on its exterior surface, combustible products of the ablation reaction in the tissue which reach the tip 116 are less likely to be ignited and cause popping.

The circulation of the saline solution through the cavity 17 also serves to cool the tip 116. This can help prevent coagulation at the exterior surface of the tip 116 and may also decrease popping by reducing the surface temperature of the tip. More specifically, heat generated in the electrode 132, the tip 116 and the ablating tissue adjacent to the tip 116 is carried away by the circulating saline solution. Preferably, the flow rate of the saline solution is between 0.3 to 1 cc/sec.

Because the saline buffer layer which surrounds the electrode 132 electrically couples the electrode 132 to the tip 116 so that the current density on the tip is relatively uniform, the catheter 100 can be operated at a relatively high power such as 50 watts with an acceptably low incidence of popping and clotting. Because the catheter 100 can be operated at a relatively high power, deeper lesions can be obtained, which is especially important in applications where thicker sections of the endocardial wall are being ablated.

The metal tip 116 may be made of a variety of metals, for example platinum, as long as the tip 116 is made of a sufficiently conductive material so that there is sufficient electrical coupling between the saline buffer layer and the interior surface of the wall of the tip 116. It is also noted that other conductive fluids may be substituted for the saline solution, as long as the conductive fluid can sufficiently carry current to effect a sufficiently uniform current distribution at the tip 116. Also, the exact composition of the saline solution can be optimized, so that it has an impedance which is high enough to prevent hot spots on the tip 116, while still remaining low enough to permit sufficient current to be communicated to the tip 116 and adjacent tissue.

Figure 4:
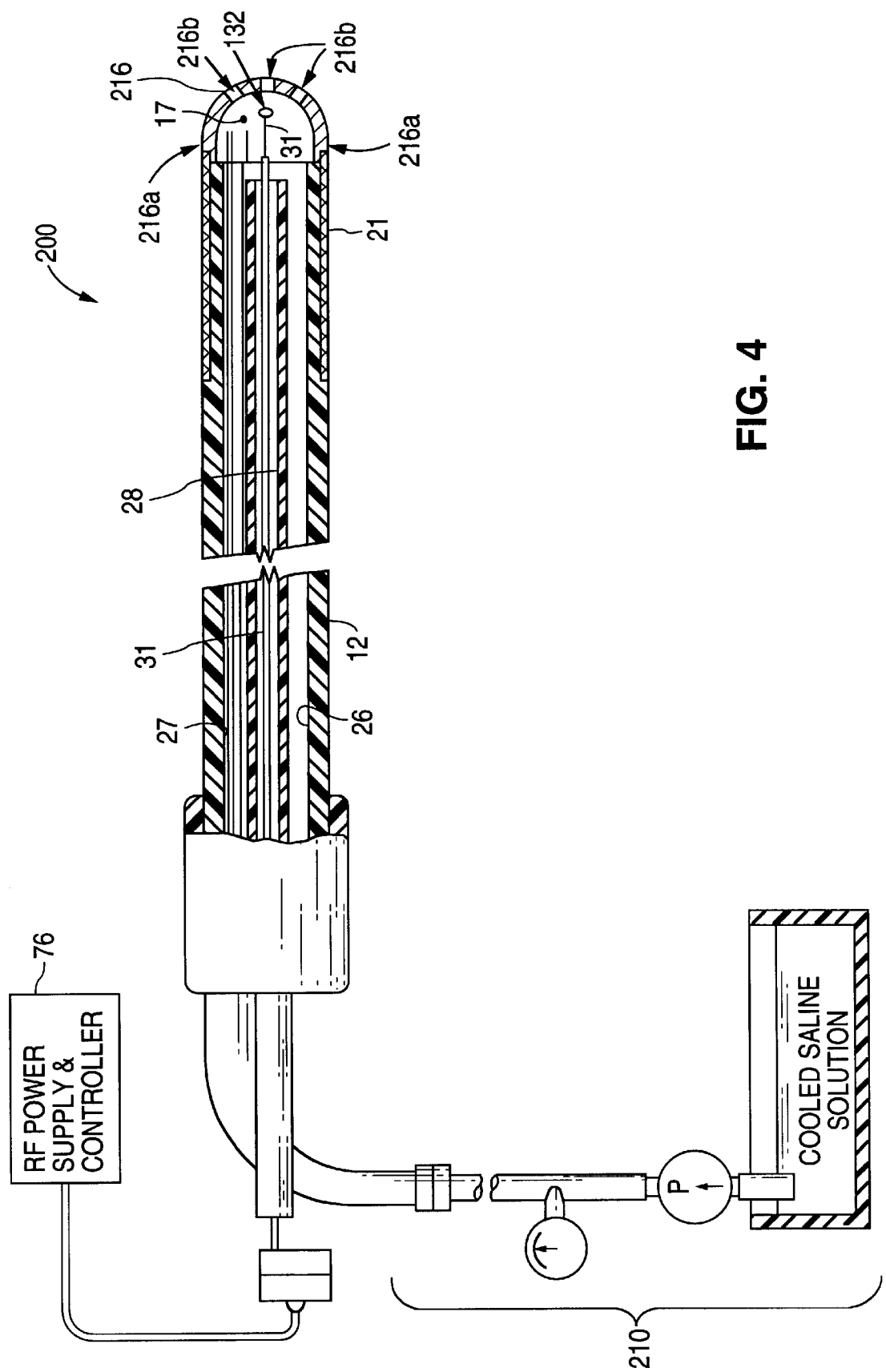
FIG. 4 shows a second embodiment an ablative tip catheter according to the present invention.

FIG. 4 shows a second embodiment of an ablative catheter 200 according to the present invention. The catheter is similar to the catheter discussed above in connection with FIG. 3, except that the saline does not circulate. Instead a one way saline pumping assembly 210 pumps saline into both lumens 26 and 27, into the cavity 17 and then out of saline flush holes 216b of tip 216 into the body. The tip 216 is rigid and cup-shaped.

In catheter 200, the saline solution buffer layer flowing through the cavity 17 will communicate RF energy through the saline flush holes 216b and directly to the tissue to be ablated. The saline solution in this embodiment provides a direct path from the electrode 132 to the surrounding tissues. Because the saline solution is continuously discharged into the body in the vicinity of the ablation, the discharged saline can provide for more cooling of the tissues being ablated, which can also assist in reducing temperatures and assist in preventing coagulation.

In the catheter 200, the electrode 132 is spaced away from the tip 216 (preferably by at least 1 millimeter) so that the saline solution in cavity 17 forms a buffer layer. The buffer layer provides a means so that combustible products of the ablation reaction which reach the tip 216 will not reach the electrode 132 and will not be ignited and popping is thereby prevented. Also, the fluid pressure of the saline solution flowing out of the saline flush holes 216b can help keep combustible products of the ablation reaction away from the tip 216 and away from electrode 132. This further reduces the possibility of igniting the combustible products.

In this embodiment, the tip 216 may be made of metal, such as platinum, or a non-conductive material, such as nylon. If the tip 216 is made of conductive metal, some of the RF energy may be communicated through the tip itself, in addition to being communicated through the saline in the saline flush holes 216b. Also, a metal tip 216 may provide for superior heat dissipation because of the relatively high thermal conductivity of a metal tip 216.

If the tip 216 is made of a non-conductive material, then the RF energy is communicated through the saline flushed through the holes in the tip 216.

It is noted that the edges of the saline flush holes 216 provide a potential area for an area of high current. Areas of high current density can be avoided by keeping the power level sufficiently low, by controlling the size and distribution of the saline flush holes 216b, and by controlling the distance between the electrode 132 and the interior wall of the tip 216.

One potential problem when using a tip 216 with saline flush holes 216b is jetting. The size of the saline flush holes 216b, the pumping pressure of the saline solution and the material of the tip 216 must be controlled to prevent adverse jetting action.

Figure 5:
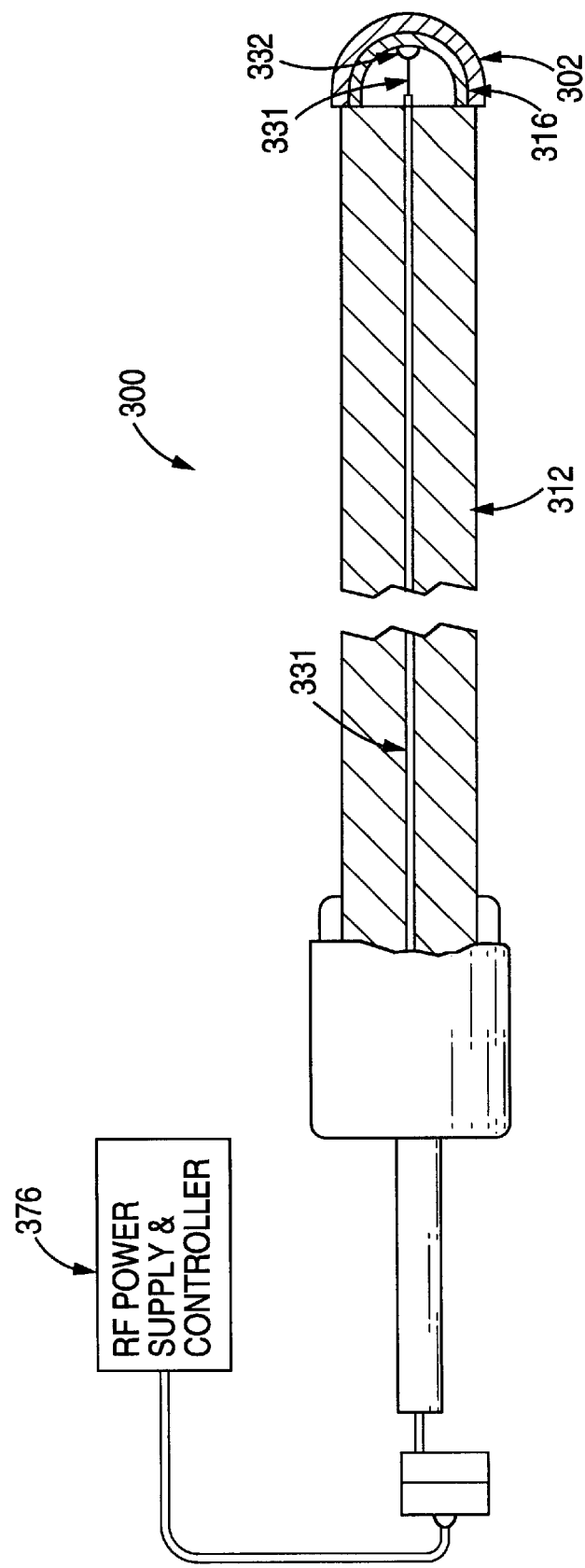
FIG. 5 shows a third embodiment of the ablative tip of an ablative tip catheter according to the present invention.

FIG. 5 shows a third embodiment of an ablation catheter assembly 300 according to the present invention. In the catheter 300, in this embodiment, there is a porous, buffer layer 302 disposed over a platinum tip electrode 316. The buffer layer 302 will communicate RF energy from the tip 316 through bodily fluid which infuses the buffer layer 302, or through fluid within the buffer layer, while helping to prevent areas of high current density at the exterior surface of the buffer layer 302, and also helping to prevent combustible by-products of the ablation reaction from reaching the surface of the metal tip electrode 316.

Catheter tip assembly 300 includes RF power supply and controller 376, elongate flexible catheter shaft 312, lead wire 331, connection 332, metal electrode tip 316 and porous buffer layer 302. During ablation, RF power supply and controller 376 supplies RF current to lead wire 331 which runs down the length of the catheter shaft 312. The current passes through the connection 332 directly to the cup-shaped, metal electrode tip 316. Connection 332 is made for example by soldering the lead wire 331 to the inner surface of the electrode tip 316.

The exterior surface of metal electrode tip 316 is completely covered by the porous buffer layer 302. RF energy is communicated through the buffer layer 302 and the blood or fluid which infuses the porous buffer layer 302.

The buffer layer 302 forms a barrier which prevents combustible by-products of the ablation reaction from reaching the exterior surface of the tip 316 so that these combustible by-products do not ignite. Meanwhile, combustible by-products of ablation which happen to reach the exterior surface of the buffer layer 302 will not tend to ignite because of the relatively uniform distribution of current effected by the buffer layer 302. These features further reduce popping. Because of the reduction in popping, it is believed that the catheter 300 can be operated at a relatively high power of up to at least 50 watts.

The effective impedance of the buffer layer 302 will be affected by both the material chosen for the buffer layer 302, as well as the extent which blood or conductive fluids can infuse the buffer layer 302 and the thickness of the buffer layer 302. The effective impedance should be low enough to allow sufficient energy transfer to the adjacent tissue so that ablation can be achieved.

Several different kinds of materials are suitable for the buffer layer 302. These suitable materials include: polymeric coatings, polymeric adhesives, polymeric foams, metallic salts, porous metal films, etched metals, metal-filled polymeric coating, metal-filled polymeric adhesives, metal-filled polymeric foams, cellulose, hydrogels and paper-type materials.

It is noted that the catheter of FIG. 5 does not necessarily employ a saline cooling system as long as the buffer layer 302 reduces hot spots and popping to obviate the need to resort to the extra expense of such a cooling system.

While preferred embodiments of the present invention have been described above using illustrative examples, it will be understood by those skilled in the art that the invention is not limited by the illustrative examples and that various changes and modifications may be made without departing from the spirit or scope of the invention as set forth in the following claims.

What is claimed is:

1. An ablation catheter assembly comprising:
   an elongate catheter shaft having a proximal end and a distal end;
   a rigid hollow tip connected to the distal end of the catheter shaft, the tip including an electrically conductive region thereon;
   a lead wire disposed within the catheter shaft;
   an electrode disposed at the distal end of the lead wire and within the hollow tip, spaced away from the interior wall surfaces of the catheter shaft and the hollow tip;
   a source of ablation energy coupled to the lead wire; and
   a source of conductive fluid coupled to the hollow tip to direct flow of conductive fluid into contact with the electrode, during use the conductive fluid forming at least a portion of a conductive path between the electrode and tissue to be ablated.

2. The ablation catheter assembly according to claim 1, wherein:
   the catheter shaft includes a lumen extending therethrough, with the lumen being adapted to carry the conductive fluid from a proximal portion of the catheter shaft to the tip and wherein the tip includes flush holes which allow passage of the conductive fluid through the tip and into contact with the tissue.

3. The ablation catheter assembly according to claim 2 wherein the conductive region of the tip is made of metal.

4. The ablation catheter assembly according to claim 3 wherein the conductive region of the tip is made of platinum.

5. The ablation catheter assembly according to claim 2, further comprising a pump for delivering the conductive fluid to the proximal end of the catheter and for pumping the conductive fluid through the lumen in the catheter shaft, into the tip and through the flush holes in the tip.

6. The ablation catheter assembly according to claim 5, further comprising a power supply for delivering radio frequency electrical energy to the lead wire and the electrode.

7. The ablation catheter assembly of claim 1 wherein the tip forms a substantially fluid-tight enclosure at the distal end of the catheter shaft so that conductive fluid flowing into the tip forms a conductive path between the electrode and the tip.

8. An ablation catheter assembly comprising:
an elongate catheter shaft having a proximal end and a distal end;
a rigid hollow tip connected to the distal end of the catheter shaft, the tip made of plastic having a fixed shape, and further including flush holes thereon;
a lead wire disposed within the catheter shaft;
an electrode disposed at the distal end of the lead wire and within the hollow tip, spaced away from the interior wall surfaces of the catheter shaft and the hollow tip;
a source of ablation energy coupled to the lead wire; and
a source of conductive fluid coupled to the hollow tip to direct flow of conductive fluid into contact with the electrode, during use the conductive fluid forming at least a portion of a conductive path between the electrode and tissue to be ablated and passing through the flush holes and into contact with the tissue.

9. The ablation catheter assembly according to claim 8 wherein the tip is made of nylon.

10. An ablation catheter assembly comprising:
an elongate catheter shaft having a distal end,
a rigid hollow tip connected to the distal end of the catheter shaft, the tip including an electrically conductive region thereon;
a lead wire disposed within the catheter shaft; and
an electrode disposed at the distal end of the lead wire and within the hollow tip, spaced away from the interior wall surfaces of the catheter shaft and the hollow tip;
a source of conductive fluid;
wherein the catheter shaft includes a first lumen defined therethrough which is adapted to carry a conductive fluid from the source of conductive fluid to the tip and wherein the catheter shaft includes a second lumen defined therethrough which is adapted to carry a conductive fluid from the tip to a proximal portion of the catheter shaft, with said tip forming a substantially fluid-tight enclosure at the distal end of the catheter shaft so that the conductive fluid will circulate from the first lumen into the tip and back through the second lumen.

11. The ablation catheter assembly according to claim 10 wherein the conductive region of the tip is made of metal.

12. The ablation catheter assembly according to claim 11 wherein the conductive region of the tip is made of platinum.

13. The ablation catheter assembly according to claim 10, further comprising a pump for delivering the conductive fluid to the first lumen at the proximal end of the catheter and for pumping the conductive fluid through the lumen in the catheter shaft, into the tip and back through the second lumen.

14. The ablation catheter assembly according to claim 13, further comprising a power supply for delivering radio frequency electrical energy to the lead wire and the electrode.

15. An ablation catheter assembly comprising:
an elongate catheter shaft having a proximal end, a distal end and a lumen defined therethrough, with the lumen being adapted to carry a conductive fluid from the proximal end of the catheter shaft to the distal end;
a rigid hollow tip connected to the distal end of the catheter shaft, the tip having a fixed shape and having flush holes formed therein which allow passage of the conductive fluid through the tip;
a lead wire disposed within the catheter shaft and terminating in the region of the tip;
an electrode disposed at the distal end of the lead wire at a location spaced away from the interior surfaces of the tip and the catheter shaft;
a source of ablation energy coupled to the lead wire; and
a source of conductive fluid coupled to the hollow tip to direct flow of conductive fluid into contact with the electrode, during use the conductive fluid forming at least a portion of a conductive path between the electrode and tissue to be ablated.

16. The ablation catheter assembly according to claim 15, further comprising:
a pump for delivering the conductive fluid to the proximal end of the catheter and for pumping the conductive fluid through the lumen in the catheter shaft, into the tip and through the flush holes in the tip; and
a power supply for delivering radio frequency electrical energy to the lead wire and the electrode.

17. An ablation catheter assembly comprising:
a source of conductive fluid
an elongate catheter shaft having a proximal portion, a distal end, a first lumen defined therethrough which is adapted to carry a conductive fluid from the source of conductive fluid to the distal end, and a second lumen defined therethrough which is adapted to carry a conductive fluid from the distal end to a proximal portion of the catheter shaft;
a rigid hollow tip connected to the distal end of the catheter shaft and forming a substantially fluid-tight enclosure at the distal end of the catheter shaft so that the conductive fluid will circulate from the first lumen into the tip and back through the second lumen, the hollow tip having an electrically conductive region thereon;
a lead wire disposed within the catheter shaft; and
an electrode connected to the distal end of the lead wire and disposed within the fluid-tight enclosure defined by the tip and being spaced away from the inner surface of the tip.

18. The ablation catheter assembly according to claim 17, further comprising:
a pump for delivering the conductive fluid to the first lumen at the proximal end of the catheter and for pumping the conductive fluid through the lumen in the catheter shaft, into the tip and back through the second lumen; and
a power supply for delivering radio frequency electrical energy to the lead wire and the electrode.

19. The ablation catheter assembly according to claim 17 wherein the electrode is further spaced away from the interior surface of the catheter shaft.

20. The ablation catheter assembly of claim 17 wherein the fluid lumen is configured to direct flow of conductive fluid into contact with the electrode so that conductive fluid flowing into the tip forms a conductive path between the electrode and the tip.

* * * * *